United States Patent
Angibaud et al.

(10) Patent No.: US 10,959,853 B2
(45) Date of Patent: Mar. 30, 2021

(54) PROSTHESIS COMPONENT WITH OFFSET ADJUSTABILITY

(71) Applicant: Exactech, Inc., Gainsville, FL (US)

(72) Inventors: Laurent Angibaud, Gainesville, FL (US); Luis Alvarez, Gainesville, FL (US)

(73) Assignee: Exactech, Inc., Gainesville, FL (US)

(*) Notice: Subject to any disclaimer, the term of this patent is extended or adjusted under 35 U.S.C. 154(b) by 273 days.

(21) Appl. No.: 15/125,441

(22) PCT Filed: Mar. 12, 2015

(86) PCT No.: PCT/US2015/020170
§ 371 (c)(1),
(2) Date: Sep. 12, 2016

(87) PCT Pub. No.: WO2015/138720
PCT Pub. Date: Sep. 17, 2015

(65) Prior Publication Data
US 2017/0172748 A1    Jun. 22, 2017

Related U.S. Application Data (60) Provisional application No. 61/951,957, filed on Mar. 12, 2014, provisional application No. 61/980,099, filed on Apr. 16, 2014.

(51) Int. Cl.
*A61F 2/38* (2006.01)
*A61F 2/30* (2006.01)

(52) U.S. Cl.
CPC ...... *A61F 2/389* (2013.01); *A61F 2002/3054* (2013.01); *A61F 2002/30331* (2013.01);
(Continued)

(58) Field of Classification Search
CPC ............. A61F 2/389; A61F 2002/3054; A61F 2002/30331; A61F 2002/30476; A61F 2002/30611
See application file for complete search history.

(56) References Cited

U.S. PATENT DOCUMENTS

| | | | | |
|---|---|---|---|---|
| 4,219,893 A | * | 9/1980 | Noiles | A61F 2/3836 623/20.25 |
| 4,301,553 A | * | 11/1981 | Noiles | A61F 2/3836 623/20.25 |

(Continued)

OTHER PUBLICATIONS

International Search report for International Application No. PCT/US2015/020170, dated Jun. 12, 2015.

*Primary Examiner* — Jacqueline Woznicki
(74) *Attorney, Agent, or Firm* — Greenberg Traurig, LLP (57) ABSTRACT

A prosthesis system of the present invention includes a monoblock stem extension including a proximal portion having a first neutral axis; and a distal portion defined by a longitudinal cylindrical shaft having a second neutral axis, wherein the second neutral axis is parallel and offset by a distance α from the first neutral axis; and an eccentric bushing arranged coaxial around the cylindrical shaft of the monoblock stem extension, the eccentric bushing including an external cylindrical shaft having a third neutral axis; and an internal cylinder having a fourth neutral axis that is substantially co-linear with the second neutral axis of the monoblock stem extension, wherein the third neutral axis is parallel and offset by a distance β from the fourth neutral axis.

20 Claims, 8 Drawing Sheets

(52) U.S. Cl.
CPC ............... *A61F 2002/30476* (2013.01); *A61F 2002/30604* (2013.01)

(56) References Cited

U.S. PATENT DOCUMENTS

| | | | | | |
|---|---|---|---|---|---|
| 5,271,737 | A | * | 12/1993 | Baldwin | A61F 2/389 623/20.34 |
| 5,290,313 | A | * | 3/1994 | Heldreth | A61F 2/389 623/20.15 |
| 5,507,818 | A | * | 4/1996 | McLaughlin | A61F 2/30734 623/23.42 |
| 5,782,920 | A | * | 7/1998 | Colleran | A61F 2/389 403/306 |
| 6,146,424 | A | * | 11/2000 | Gray, Jr. | A61F 2/389 623/20.15 |
| 6,162,255 | A | * | 12/2000 | Oyola | A61F 2/389 623/20.15 |
| 6,214,052 | B1 | * | 4/2001 | Burkinshaw | A61F 2/389 623/20.15 |
| 6,290,726 | B1 | * | 9/2001 | Pope | A61F 2/30767 623/18.11 |
| 7,998,217 | B1 | * | 8/2011 | Brown | A61F 2/3609 623/20.14 |
| 8,491,587 | B2 | | 7/2013 | McGovern et al. | |
| 2003/0014120 | A1 | | 1/2003 | Carson et al. | |
| 2003/0158606 | A1 | * | 8/2003 | Coon | A61F 2/38 623/20.15 |
| 2009/0125114 | A1 | * | 5/2009 | May | A61B 17/1764 623/20.14 |
| 2009/0149963 | A1 | | 6/2009 | Sekel | |

\* cited by examiner

PROSTHESIS COMPONENT WITH OFFSET ADJUSTABILITY

RELATED APPLICATIONS

This application is a 35 U.S.C. § 371 national stage application of International Patent Application Serial No. PCT/US2015/020170, filed on Mar. 12, 2015, which claims priority to U.S. Provisional Patent Application Ser. No. 61/951,957, filed on Mar. 12, 2014, and U.S. Provisional Patent Application Ser. No. 61/980,099, filed on Apr. 16, 2014 the entire contents of which are incorporated by reference in their entirety.

This application claims priority to, and the benefit of, U.S. Provisional Application No. 61/951,957, filed Mar. 12, 2014 and U.S. Provisional Application No. 61/980,099, filed Apr. 16, 2014. The contents of each of these applications are incorporated herein by reference in their entirety.

BACKGROUND

The anatomy of the human tibia is quite variable with respect to the position of the intramedullary canal relative to the proximal tibia. As a consequence of this variability, a tibial stem which is centrally located on the tibial baseplate could interfere with the cortex as a surgeon attempts to center the tibial baseplate on the proximal cut tibia. This anatomical variation is known as the tibial offset.

SUMMARY

Prosthesis components with offset adjustability are disclosed herein.

According to aspects illustrated herein, there is disclosed a prosthesis system of the present invention that includes a monoblock stem extension comprising a proximal portion having a first neutral axis; and a distal portion defined by a longitudinal cylindrical shaft having a second neutral axis, wherein the second neutral axis is parallel and offset by a distance $\alpha$ from the first neutral axis; and an eccentric bushing arranged coaxial around the cylindrical shaft of the monoblock stem extension, the eccentric bushing comprising an external cylindrical shaft having a third neutral axis; and an internal cylinder having a fourth neutral axis that is substantially co-linear with the second neutral axis of the monoblock stem extension, wherein the third neutral axis is parallel and offset by a distance $\beta$ from the fourth neutral axis.

According to aspects illustrated herein, there is disclosed a kit of the present invention that includes a first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; and at least two bushings of the present invention available under multiple diameter options and multiple lengths.

According to aspects illustrated herein, there is disclosed a kit of the present invention that includes first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; a first bushing of the present invention; and a second eccentric bushing of the present invention, wherein the center of the circle formed by the outside diameter of the external cylindrical shaft of the second eccentric bushing is at a different point from the center of the circle formed by the inside diameter of the internal cylinder of the second eccentric bushing so the two circles are not concentric.

According to aspects illustrated herein, there is disclosed a kit of the present invention that includes first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; at least two first bushings of the present invention available under multiple diameter options and multiple lengths; and at least two second eccentric bushings of the present invention available under multiple lengths, wherein the center of the circle formed by the outside diameter of the external cylindrical shaft of the second eccentric bushing is at a different point from the center of the circle formed by the inside diameter of the internal cylinder of the second eccentric bushing so the two circles are not concentric.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

While this disclosure is particularly suitable for modular tibial baseplate components having modular stem extensions, the features of this invention could be adapted, as appropriate, to other prosthetic components (e.g., femoral prosthesis and humeral prosthesis) which utilize modular stem components. Towards this end, it is understood that the term "distal" and "proximal" relate to the tibial application. For example, in case of adaptation of this disclosure to a knee femoral component, then the term "distal" would be "proximal" and vice versa.

Figure 1:
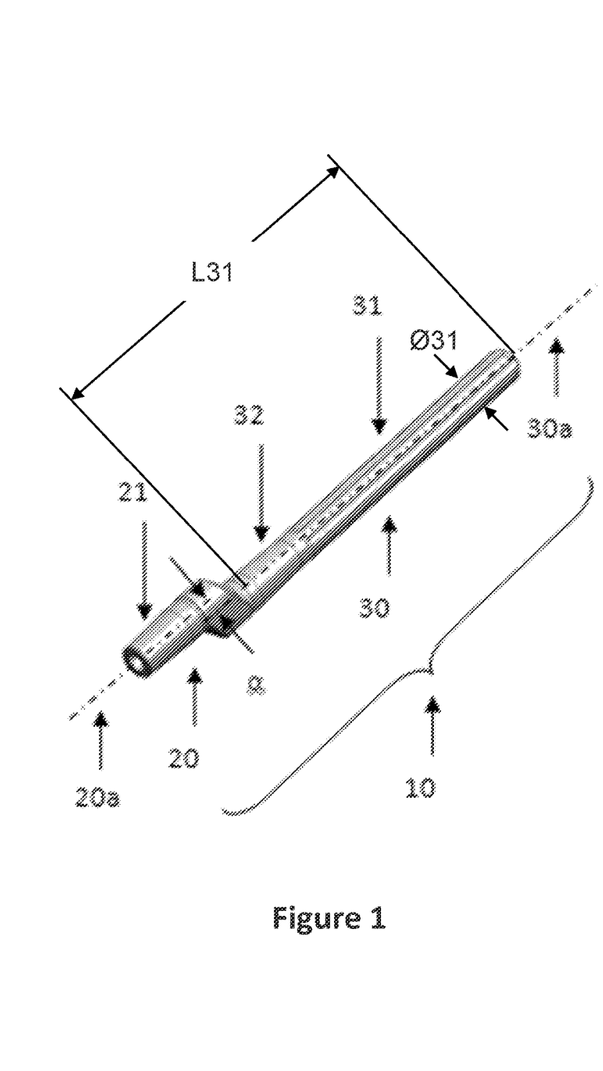
FIG. 1 shows an embodiment of a monoblock offset stem extension of the present invention.

FIG. 1 illustrates an embodiment of a monoblock offset stem extension (10) of the present invention. Monoblock offset stem extension (10) features a proximal portion (20) and a distal portion (30). The proximal portion (20) has a first neutral axis (20a). The distal portion (30) is defined by a longitudinal cylindrical shaft (31) having a second neutral axis (30a), parallel, but offset by a distance α from the first neutral axis (20a). In an embodiment, the distal portion (30) has a locking element (32). In an embodiment, the monoblock stem extension (10) is an integral component of a prosthesis. In an embodiment, the monoblock stem extension (10) is a modular component of a prosthesis. In an embodiment, the proximal portion features a locking element (21) intended to be selectively locked with a baseplate element of a prosthesis system, such as a tibial baseplate (not represented). The distance α of the monoblock offset stem element (10) can be used to correct a tibial baseplate position in the transverse plane, preferably medially or laterally. In an embodiment, the first neutral axis (20a) and the second neutral axis (30a) are offset from each other by a distance α of between about 1 mm to about 10 mm. In an embodiment, the first neutral axis (20a) and the second neutral axis (30a) are offset from each other by a distance α of between about 2 mm to about 7 mm. In an embodiment, the first neutral axis (20a) and the second neutral axis (30a) are offset from each other by a distance α of between about 3 mm to about 6 mm. In an embodiment, the first neutral axis (20a) and the second neutral axis (30a) are offset from each other by a distance α of about 1 mm. In an embodiment, the first neutral axis (20a) and the second neutral axis (30a) are offset from each other by a distance α of about 2 mm. In an embodiment, the first neutral axis (20a) and the second neutral axis (30a) are offset from each other by a distance α of about 3 mm. In an embodiment, the first neutral axis (20a) and the second neutral axis (30a) are offset from each other by a distance α of about 4 mm. In an embodiment, the first neutral axis (20a) and the second neutral axis (30a) are offset from each other y a distance α of about 5 mm. In an embodiment, the first neutral axis (20a) and the second neutral axis (30a) are offset from each other by a distance α of about 6 mm. In an embodiment, the first neutral axis (20a) and the second neutral axis (30a) are offset from each other by a distance α of about 7 mm. In an embodiment, the first neutral axis (20a) and the second neutral axis (30a) are offset from each other by a distance α of about 8 mm. In an embodiment, the first neutral axis (20a) and the second neutral axis (30a) are offset from each other by a distance α of about 9 mm. In an embodiment, the first neutral axis (20a) and the second neutral axis (30a) are offset from each other by a distance α about 10 mm. The cylindrical shaft (31) of the monoblock offset stem extension (10) is characterized by its length (L31) as well as its diameter (Ø31). In an embodiment, the diameter (Ø31) is about 5 mm to about 15 mm while the length (L31) is about 30 mm to 230 mm. In an embodiment, the diameter (Ø31) is selected from one of about 5 mm, about 6 mm, about 7 mm, about 8 mm, about 9 mm, about 10 mm, about 11 mm, about 12 mm, about 13 mm, about 14 mm, or about 15 mm. In an embodiment, the length (L31) is selected from one of about 30 mm, about 40 mm, about 50 mm, about 60 mm, about 70 mm, about 80 mm, about 90 mm, about 100 mm, about 100 mm, about 120 mm, about 130 mm, about 140 mm, about 150 mm, about 160 mm, about 170 mm, about 180 mm, about 190 mm, about 200 mm, about 210 mm, about 220 mm or about 230 mm.

Figure 2:
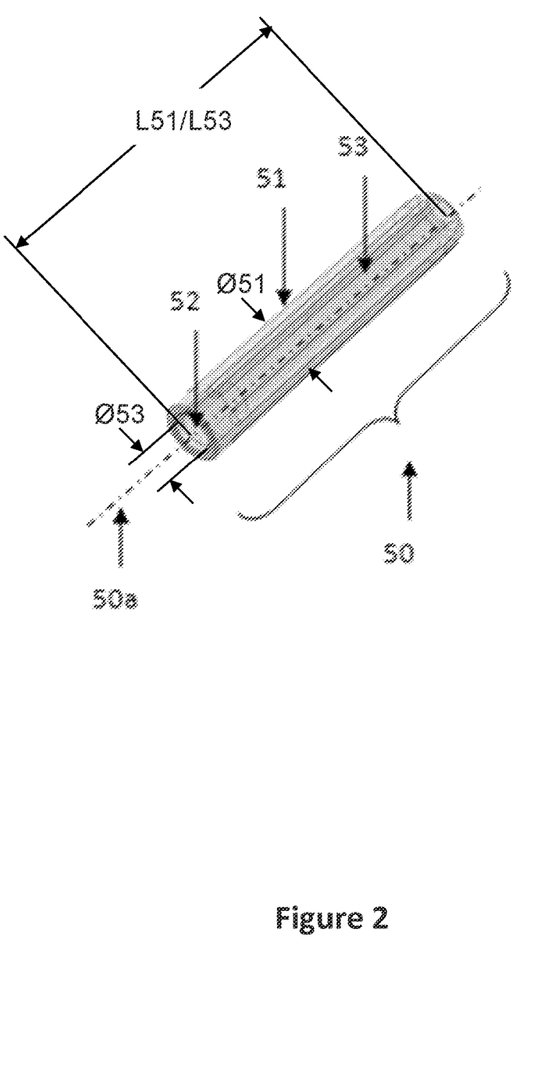
FIG. 2 shows a representative bushing of the present invention.
Figure 3A:
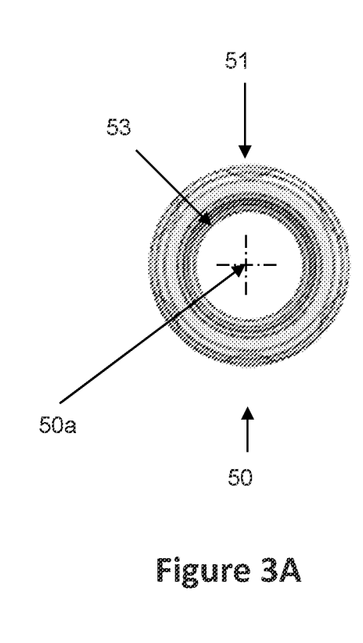
FIGS. 3A and 3B are transverse views showing a first embodiment of a bushing of the present invention (FIG. 3A) and a second embodiment of an eccentric bushing of the present invention (FIG. 3B).
Figure 3B:
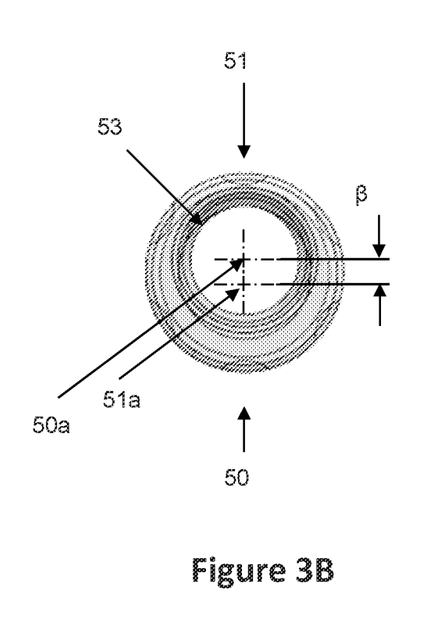

A representative bushing of the present invention is illustrated in FIG. 2. Bushing (50) features an external cylindrical shaft (51) having a neutral axis and an internal cylinder (53) having a neutral axis. In the embodiment illustrated in FIG. 2 and FIG. 3A, the neutral axis of the external cylindrical shaft (51) and the internal cylinder (53) overlap, as identified as neutral axis (50a). In the embodiment illustrated in FIG. 3B, a neutral axis (51a) of the external cylindrical shaft (51) is parallel but offset by a distance β from a neutral axis (50a) of the internal cylinder (53). The bushing (50) may further include an internal locking element (52). The external cylindrical shaft (51) of the bushing (50) is characterized by a length (L51) as well as a diameter (Ø51) and the internal cylinder (53) of the bushing (50) is characterized by a length (L53) as well as a diameter (Ø53). In an embodiment, the diameter (Ø51) is about 8 mm to about 24 mm while the length (L51) is about 20 mm to 220 mm. In an embodiment, the length (L51) of the external cylindrical shaft (51) and the length (L53) of the internal cylinder (53) are equal. In an embodiment, the diameter (Ø51) of the bushing (50) is selected from one of about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm or about 24 mm. In an embodiment, the length (L51) of the external cylindrical shaft (51) is selected from one of about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, about 200 mm, about 210 mm or about 220 mm.

In an embodiment, the length (L51) of the external cylindrical shaft (51) of the bushing (50) is smaller than the length (L31) of the cylindrical shaft (31) of the monoblock offset stem extension (10).

Figure 4:
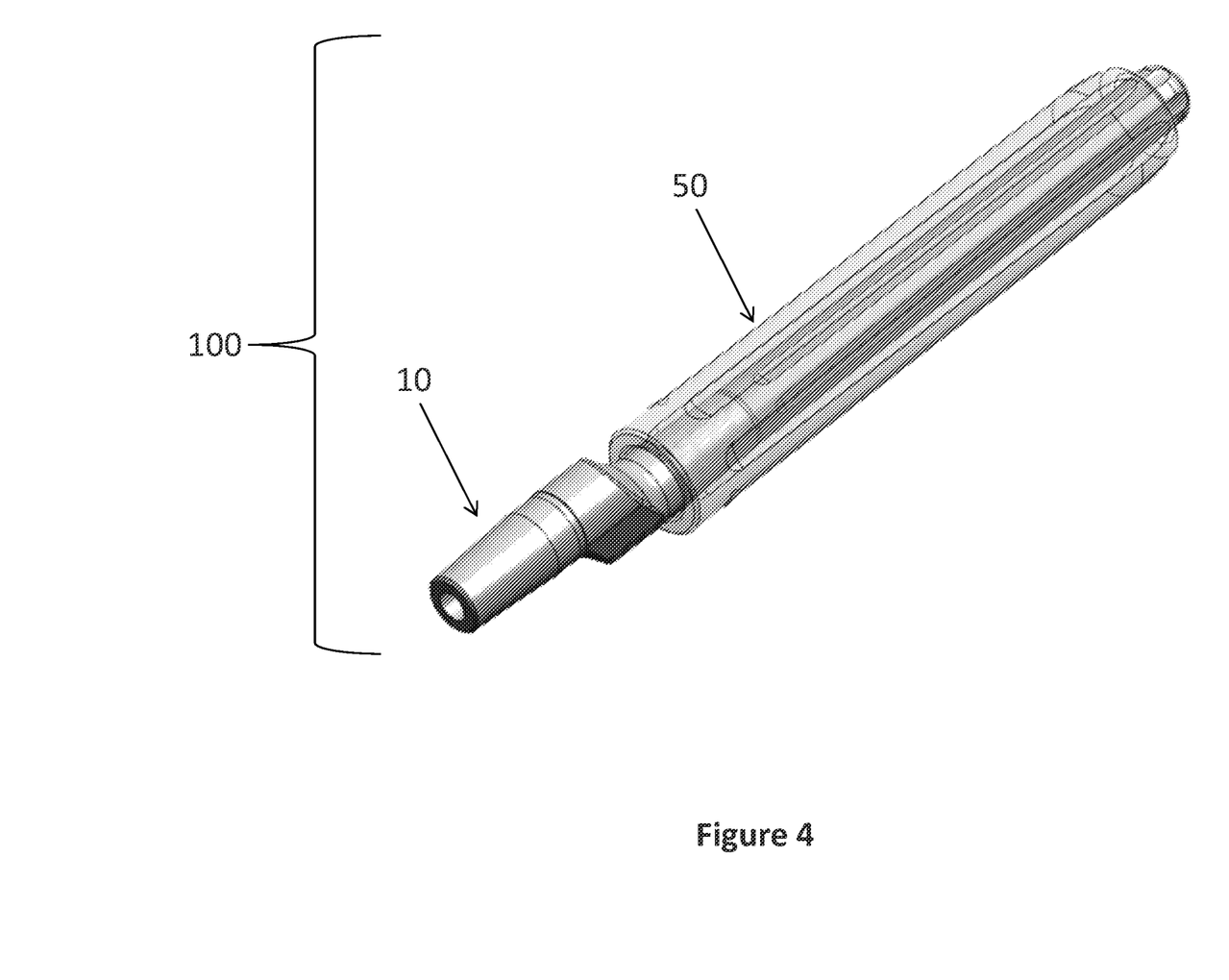
FIG. 4 shows an embodiment of a prosthesis system of the present invention with a monoblock stem extension and a bushing.

As illustrated in FIG. 4, together a monoblock offset stem element (10) of the present invention and a bushing (50) of the present invention form a prosthesis system (100) of the present invention. The usage of the prosthesis system (100)

depends of the diameter of the intramedullary canal of a patient's long bone. In an embodiment, the prosthesis system of the present invention achieve optimal fit of prosthesis components while still reducing the inventory of joint prosthesis parts that are needed to meet patient needs. Regarding inventory, in an embodiment a kit of the present invention includes monoblock stem extensions available under (Z) offset options as well as bushings available under (Y) diameter options and (X) lengths. In an embodiment, a component set of the present invention requires (X*Y+Z) components.

In an embodiment, a kit of the present invention includes a first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; and at least two bushings of the present invention available under multiple diameter options and multiple lengths.

In an embodiment, a kit of the present invention includes first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; a first bushing of the present invention; and a second eccentric bushing of the present invention, wherein the center of the circle formed by the outside diameter of the external cylindrical shaft of the second eccentric bushing is at a different point from the center of the circle formed by the inside diameter of the internal cylinder of the second eccentric bushing so the two circles are not concentric.

In an embodiment, a kit of the present invention includes first monoblock stem extension of the present invention having a second neutral axis that is offset from a first neutral axis by a distance $\alpha_1$; a second monoblock stem extension of the present invention having a second neutral axis that is offset from a first neutral axis by a distance $\alpha_2$, wherein $\alpha_1$ and $\alpha_2$ are not equal; at least two first bushings of the present invention available under multiple diameter options and multiple lengths; and at least two second eccentric bushings of the present invention available under multiple lengths, wherein the center of the circle formed by the outside diameter of the external cylindrical shaft of the second eccentric bushing is at a different point from the center of the circle formed by the inside diameter of the internal cylinder of the second eccentric bushing so the two circles are not concentric.

In an embodiment, a surgeon selects a bushing from a kit that features a diameter similar to the diameter of the intramedullary canal of the patient's tibia and assembles it to a monoblock offset stem extension. In an embodiment, a locking element of the bushing is designed to match a locking element of the monoblock offset stem extension). Also, the internal cylinder of the bushing is compatible with the external cylinder of the monoblock offset stem extension. Finally, the length of the external cylindrical shaft of the bushing is preferably shorter than the length of the cylindrical shaft of the monoblock offset stem extension, so the distal extremity of the cylindrical shaft can protrude from the distal extremity from the external cylindrical shaft.

Figure 5A:
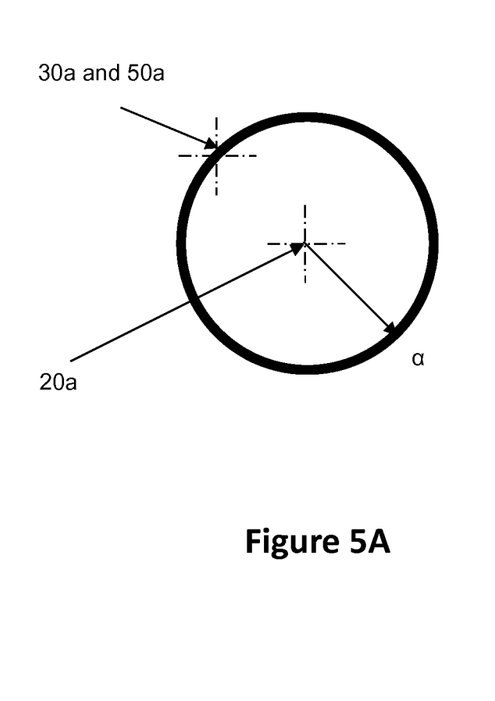
FIGS. 5A and 5B show the range of adjustment of the offset for the bushing of the first embodiment of the present invention and the eccentric bushing of the second embodiment of the present invention.
Figure 5B:
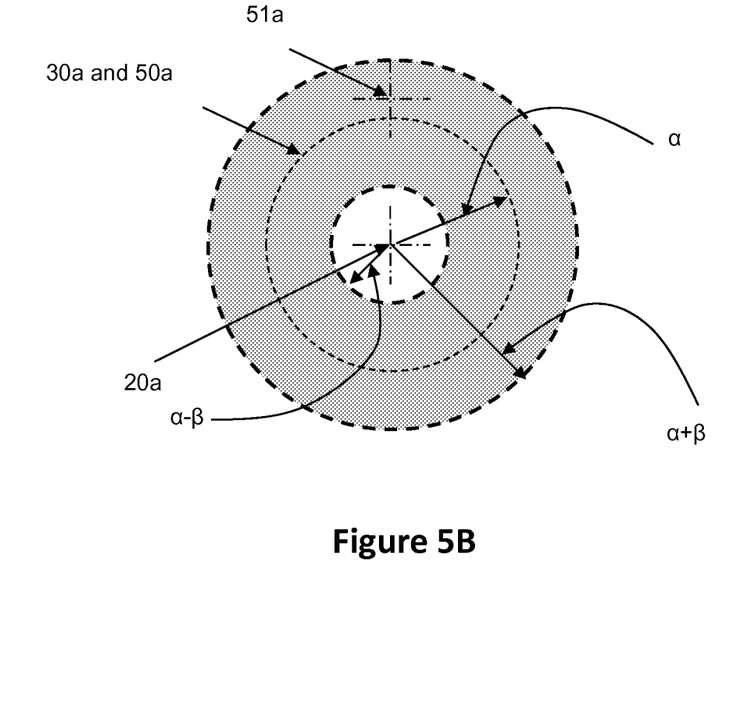

FIGS. 5A and 5B show the range of adjustment of the offset for the bushing of the first embodiment of the present invention and the eccentric bushing of the second embodiment of the present invention. In FIG. 5B, an eccentric bushing (50) illustrated in which the external cylindrical shaft (51) of the bushing (50) features a neutral axis (51a) parallel but offset by a distance β from the neutral axis (50a) defined by the internal cylinder (53) of the bushing (50). Such situation is particularly advantageous as both offsets α and β can be added or subtracted in order to adjust the offset of the anatomical long bone. In an embodiment, bushing (50) is positioned over the longitudinal cylindrical shaft (31) of the monoblock offset stem element (10) in a first position and then rotated around the longitudinal cylindrical shaft (31) to a second position so as to result in an offset that is equal to α+β. In an embodiment, bushing (50) is positioned over the longitudinal cylindrical shaft (31) of the monoblock offset stem element (10) in a first position and then rotated around the longitudinal cylindrical shaft (31) to a second position so as to result in an offset that is equal to α−β. An eccentric bushing (50) of the present invention is one which has the center of the circle formed by the outside diameter of the external cylindrical shaft (51) which is at a different point from the center of the circle formed by the inside diameter of the internal cylinder (53), so the two circles are not concentric. Eccentricity can be checked by determining the wall thickness around the bushing (50) at any cross section to establish maximum and minimum.

In an embodiment, the neutral axis (50a) and the neutral axis (51a) are offset from each other by a distance β of between about 0.25 mm to about 5 mm. In an embodiment, the neutral axis (50a) and the neutral axis (51a) are offset from each other by a distance β of about 0.25 mm. In an embodiment, the neutral axis (50a) and the neutral axis (51a) are offset from each other by a distance β of about 0.50 mm. In an embodiment, the neutral axis (50a) and the neutral axis (51a) are offset from each other by a distance β of about 0.75 mm. In an embodiment, the neutral axis (50a) and the neutral axis (51a) are offset from each other by a distance β of about 1 mm. In an embodiment, the neutral axis (50a) and the neutral axis (51a) are offset from each other by a distance β of about 1.25 mm. In an embodiment, the neutral axis (50a) and the neutral axis (51a) are offset from each other by a distance β of about 1.5 mm. In an embodiment, the neutral axis (50a) and the neutral axis (51a) are offset from each other by a distance β of about 1.75 mm. In an embodiment, the neutral axis (50a) and the neutral axis (51a) are offset from each other by a distance β of about 2 mm. In an embodiment, the third axis (50a) and the neutral axis (51a) are offset from each other by a distance β of about 2.25 mm. In an embodiment, the neutral axis (50a) and the neutral axis (51a) are offset from each other by a distance β of about 2.5 mm. In an embodiment, the neutral axis (50a) and the neutral axis (51a) are offset from each other by a distance β of about 2.75 mm. In an embodiment, the neutral axis (50a) and the neutral axis (51a) are offset from each other by a distance β of about 3 mm. In an embodiment, the neutral axis (50a) and the neutral axis (51a) are offset from each other by a distance β of about 3.25 mm. In an embodiment, the neutral axis (50a) and the neutral axis (51a) are offset from each other by a distance β of about 3.5 mm. In an embodiment, the neutral axis (50a) and the neutral axis (51a) are offset from each other by a distance β of about 3.75 mm. In an embodiment, the neutral axis (50a) and the neutral axis (51a) are offset from each other by a distance β of about 4 mm. In an embodiment, the neutral axis (50a) and the neutral axis (51a) are offset from each other by a distance β of about 4.25 mm. In an embodiment, the neutral axis (50a) and the neutral axis (51a) are offset from each other by a distance β of about 4.5 mm. In an embodiment, the neutral axis (50a) and the neutral axis (51a) are offset from each other by a distance β of about 4.75 mm. In an embodiment, the neutral axis (50a) and the neutral axis (51a) are offset from each other by a distance β of about 5 mm.

With respect to FIG. 5A, in an embodiment the neutral axis (50a) of the bushing (50) or the neutral axis (30a) of the cylindrical shaft (31) can rotate around the neutral axis (20a) of the first locking element (21) by an offset of α. With respect to FIG. 5B, in an embodiment the neutral axis (51a) of bushing (50) can rotate around the neutral axis (50a) of the internal cylinder (53) by an offset of β; which is substantially co-linear with the neutral axis (30a) of the cylindrical shaft (31); which can itself rotate around the neutral axis (20a) of the proximal portion (20) by an offset of α; which results into the neutral axis (51a) of bushing (50) being located relative to the neutral axis (20a) of the proximal portion (20) inside an area defined by α±β.

If α=β, then the combination of the monoblock offset stem extension (10) with the bushing (50) allows the full adjustment of the offset inside a circle having a radius of α+β. Such eccentric bushing (50) is particularly appealing from inventory, as the system monoblock stem extension available under 1 offset option as well as bushing available under (Y) diameter options and (X) length. In an embodiment, a component set of the present invention requires (X*Y+1) components.

According to another embodiment, a locking element (not represented) can be added (preferably at the distal extremity) to the cylindrical shaft (31) of the monoblock stem extension (10) in order to fully assemble the locking elements.

Figures 6A, 6B:
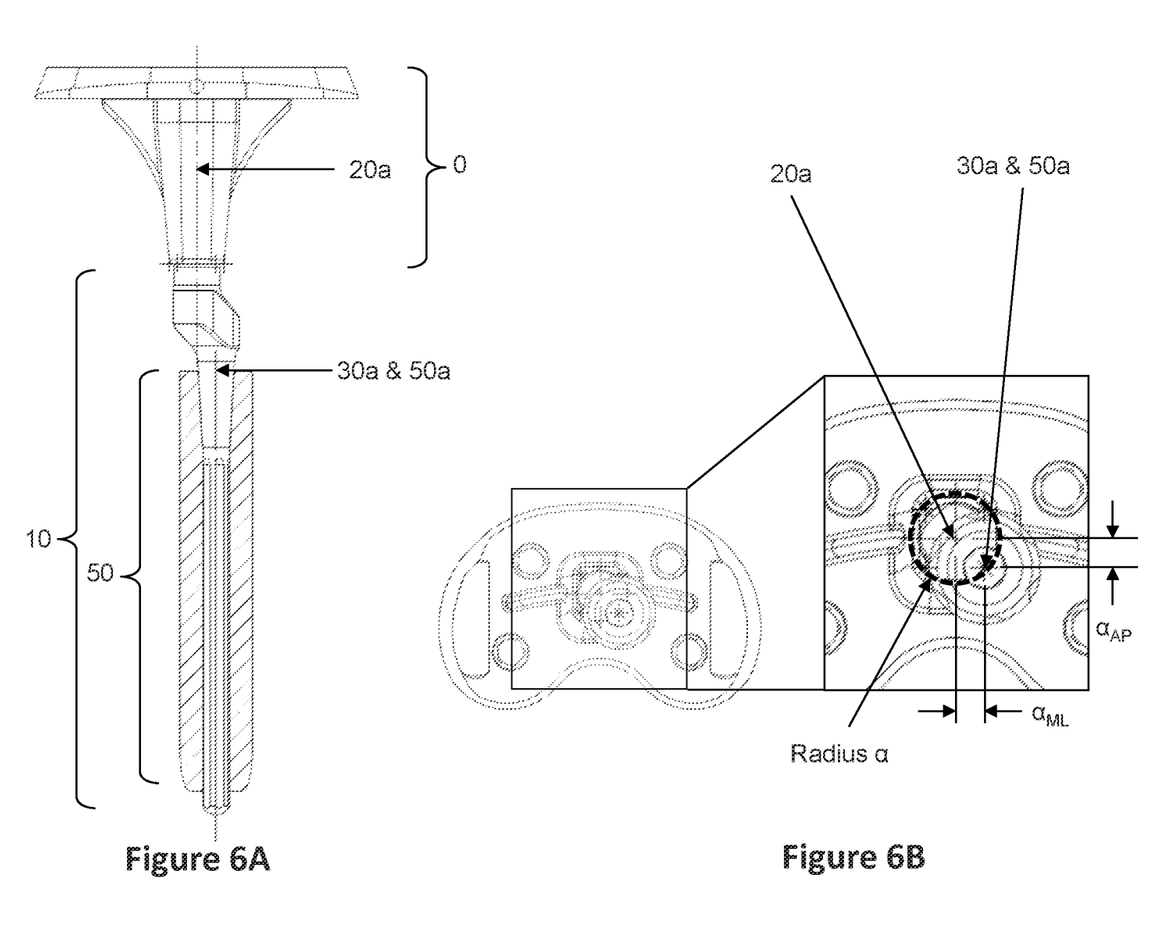
FIGS. 6A and 6B show random positions of a component system of a first embodiment of the present invention assembled with a tibial tray.
Figure 6C:
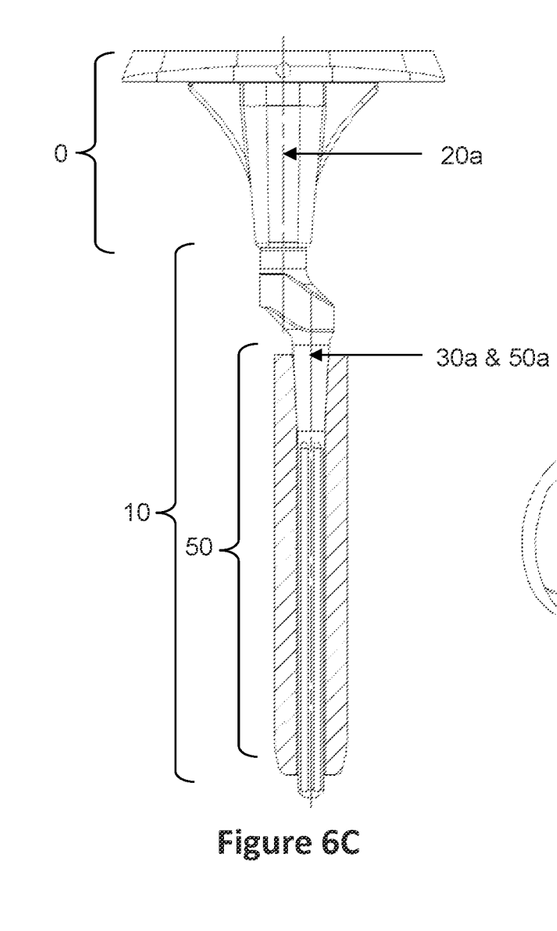
FIGS. 6C and 6D show random positions of a component system of a first embodiment of the present invention assembled with a tibial tray.
Figure 6D:
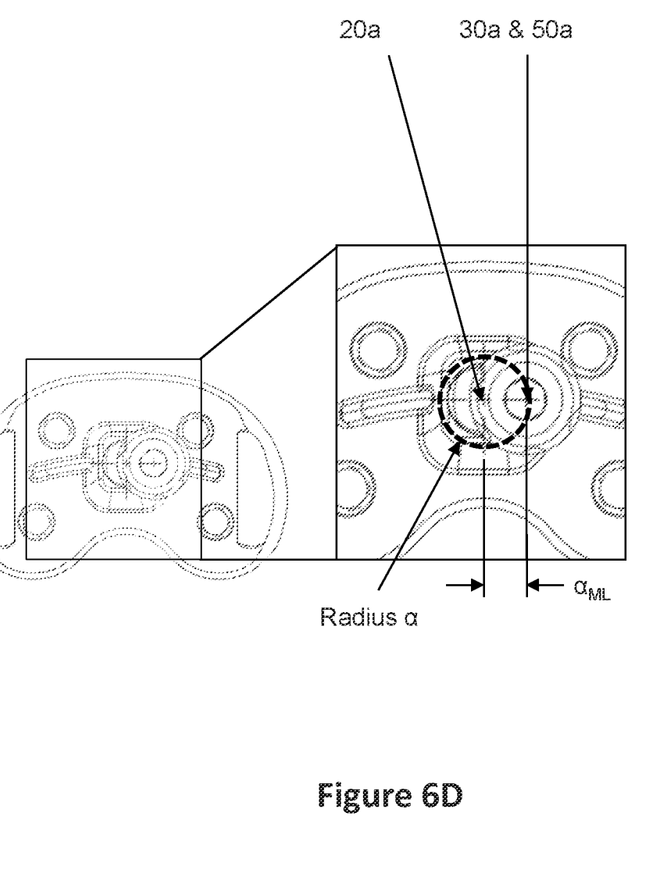

FIGS. 6A, 6B, 6C and 6D are representations of random positions of the component system assembled with a tibial tray (0). Due to the offset (α) between the first neutral axis (20a) of the proximal portion (20) and the second neutral axis (30a) of the longitudinal cylindrical shaft (31) then the second neutral axis (30a) of the longitudinal cylindrical shaft (31) and the third neutral axis (50a) of the internal cylinder (53) of the bushing (50) is located on a circle centered on the first neutral axis (20a) of the proximal portion (20) of the monoblock stem extension; which the circle has a radius equal to α. Towards this end, FIGS. 6A and 6B represent a singular position where the third neutral axis (50a) of the internal cylinder (53) of the bushing (50) adjusts a tibial offset from both an antero-posterior ($\alpha_{AP}$) and medio-lateral ($\alpha_{ML}$) point of views. FIGS. 6C and 6D represent a singular position where the third neutral axis (50a) internal cylinder (53) of the bushing (50) is fully shifted along the medial or lateral aspect ($\alpha_{ML}$) depending on the side of the implant (i.e., Left or Right).

Figure 7A:
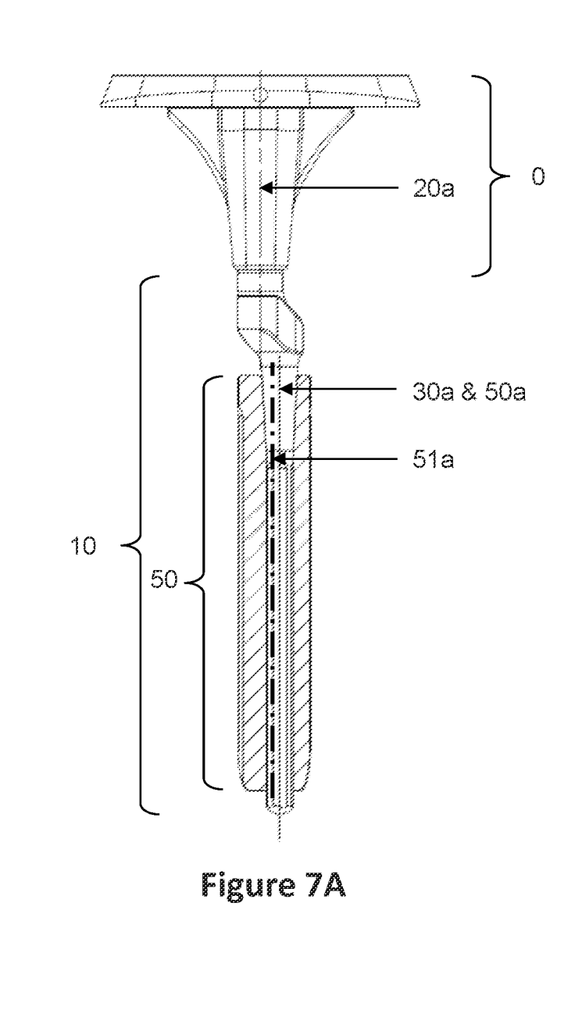
FIGS. 7A and 7B show random positions of a component system of a second embodiment of the present invention assembled with a tibial tray.
Figure 7B:
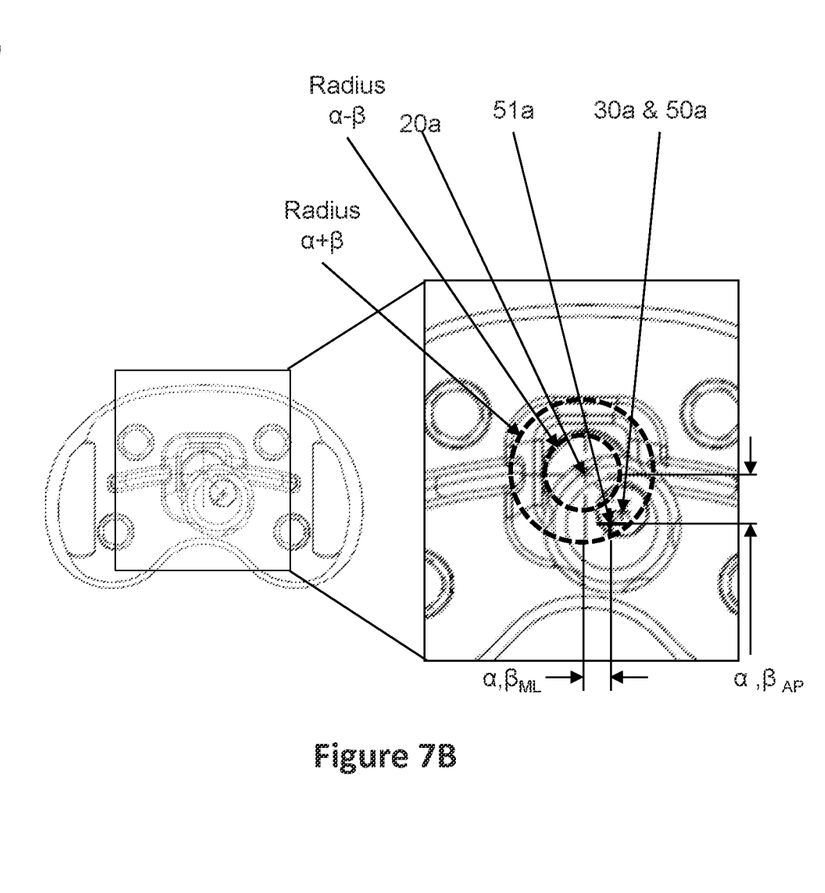
Figure 7C:
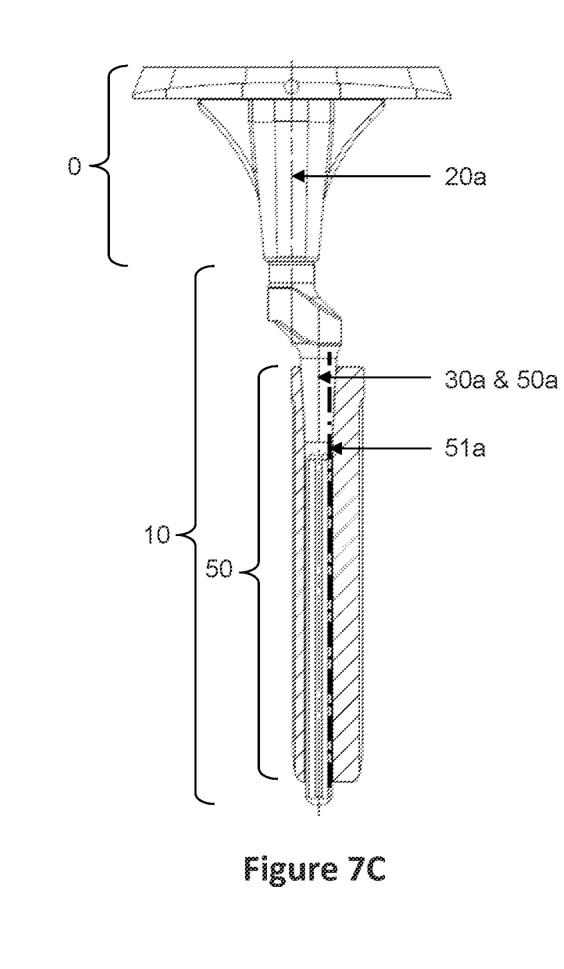
FIGS. 7C and 7D show random positions of a component system of a second embodiment of the present invention assembled with a tibial tray.
Figure 7D:
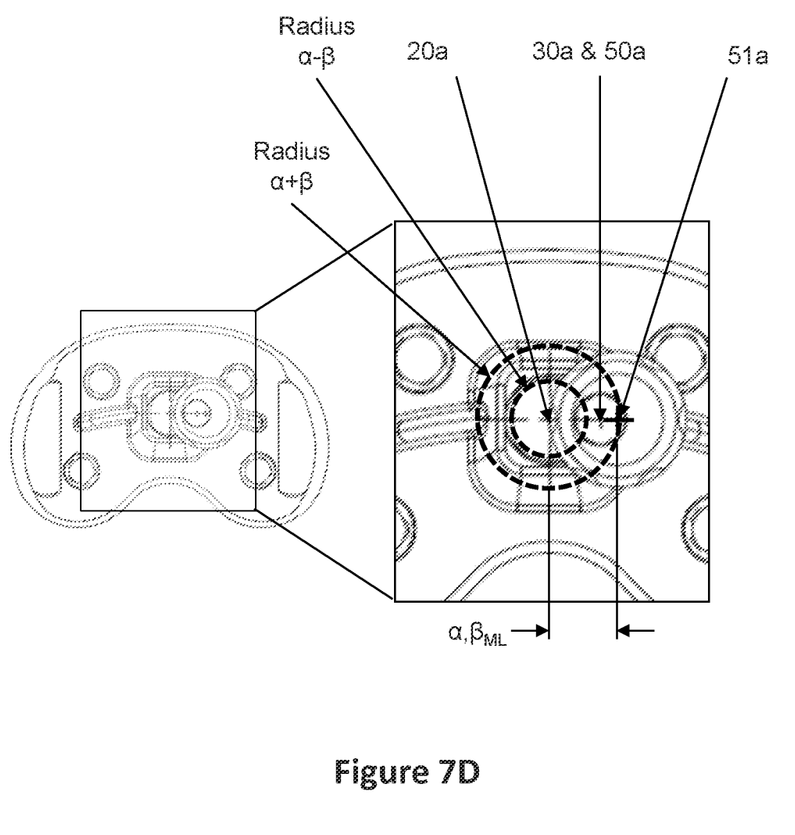

FIGS. 7A, 7B, 7C and 7D are representations of random positions of the component system assembled with a tibial tray (0). Due to the combined presence of the offset (α) between the first neutral axis (20a) of the proximal portion (20) and the second neutral axis (30a) longitudinal cylindrical shaft (31) and the offset (β) between the third neutral axis (50a) of the internal cylinder (53) of the eccentric bushing (50), then the fourth neutral axis (51a) of the external cylindrical shaft (51) of the bushing (50) is located between two concentric circles centered on the first neutral axis (20a) of the proximal portion (20); which the largest circle has a radius equal to α+β and the smallest circle has a radius equal to α−=. Towards this end, FIGS. 7A and 7B represent a position where the fourth neutral axis (51a) of the external cylindrical shaft (51) of the bushing (50) adjusts a tibial offset from both an antero-posterior ($\alpha,\beta_{AP}$) and medio-lateral ($\alpha,\beta_{ML}$) point of views. FIGS. 7C and 7D represent a singular position where the fourth neutral axis (51a) of the external cylindrical shaft (51) of the bushing (50) is fully shifted along the medial or lateral aspect ($\alpha,\beta_{ML}$) depending of the side of the implant (i.e., Left or Right). Considering this singular position, the fourth neutral axis (51a) of the external cylindrical shaft (51) of the bushing (50) is located on the largest circle having a radius equal to α+β so offset ($\alpha,\beta_{ML}$) is equal to α+β. From this point it is understood that one advantage of the eccentric bushing over the first embodiment bushing is to adjust the antero-posterior tibial offset ($\alpha,\beta_{AP}$) independently of the medio-lateral offset ($\alpha,\beta_{ML}$).

A prosthesis system of the present invention includes a monoblock stem extension comprising a proximal portion having a first neutral axis; and a distal portion defined by a longitudinal cylindrical shaft having a second neutral axis, wherein the second neutral axis is parallel and offset by a distance α from the first neutral axis; and an eccentric bushing arranged coaxial around the cylindrical shaft of the monoblock stem extension, the eccentric bushing comprising an external cylindrical shaft having a third neutral axis; and an internal cylinder having a fourth neutral axis that is substantially co-linear with the second neutral axis of the monoblock stem extension, wherein the third neutral axis is parallel and offset by a distance β from the fourth neutral axis.

In an embodiment, a kit includes at least two monoblock stem extensions of the present invention, wherein the first monoblock stem extension has a distance $\alpha_1$, and wherein the second monoblock stem extension has a distance $\alpha_2$; wherein $\alpha_1$ is not equal to $\alpha_2$, and at least two bushings each having a fourth neutral axis parallel but offset by a distance β from the third neutral axis, available under multiple diameter options and multiple lengths.

While this invention is particularly suitable for tibial prosthesis components having modular stem extensions, the features of this invention could be adapted, as appropriate, to tibial prosthesis components having an integral stem extension with offset features, or other prosthetic components which utilize modular or integral stem components.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A kit, comprising:
    a first monoblock stem extension comprising:
        a proximal portion having a first neutral axis; and
        a distal portion defined by a longitudinal cylindrical shaft having a second neutral axis, wherein the second neutral axis is parallel to and offset by a distance $\alpha_1$ from the first neutral axis;
    a second monoblock stem extension comprising:
        a proximal portion having a first neutral axis; and
        a distal portion defined by a longitudinal cylindrical shaft having a second neutral axis, wherein the second neutral axis is parallel to and offset by a distance $\alpha_2$ from the first neutral axis, the distance $\alpha_2$ being unequal to the distance $\alpha_1$;
    a first eccentric bushing configured to be arranged coaxial around the cylindrical shaft of a selected one of the first or second monoblock stem extensions, the first eccentric bushing comprising:

an external cylindrical shaft having a third neutral axis; and an internal cylinder having a fourth neutral axis that is co-linear with the second neutral axis of the monoblock stem extension, wherein the third neutral axis is parallel to and offset by a distance $\beta_1$ from the fourth neutral axis, wherein the first eccentric bushing is sized and shaped to fit within an intramedullary canal of a long bone of a patient, and wherein the first eccentric bushing has a length that is greater than an outside diameter of the first eccentric bushing; and a second eccentric bushing configured to be arranged coaxial around the cylindrical shaft of a selected one of the first or second monoblock stem extensions, the second eccentric bushing comprising:

an external cylindrical shaft having a third neutral axis; and an internal cylinder having a fourth neutral axis that is co-linear with the second neutral axis of the monoblock stem extension, wherein the third neutral axis is parallel to and offset by a distance $\beta_2$ from the fourth neutral axis, the distance $\beta_2$ being unequal to the distance $\beta_1$, wherein the second eccentric bushing is sized and shaped to fit within an intramedullary canal of a long bone of a patient, and wherein the second eccentric bushing has a length that is greater than an outside diameter of the second eccentric bushing, wherein (a) the offset between the first neutral axis and the second neutral axis and (b) the offset between the third neutral axis and the fourth neutral axis are configured to enable independent adjustment of a first offset in a first direction and a tibial second offset in a second direction that is perpendicular to the first direction.

2. The kit of claim 1, wherein the first offset is an antero-posterior tibial offset, and wherein the second offset is a medio-lateral tibial offset.

3. A prosthesis system comprising:
a monoblock stem extension comprising:
a proximal portion having a first neutral axis; and
a distal portion defined by a longitudinal cylindrical shaft having a second neutral axis, wherein the second neutral axis is parallel to and offset by a distance $\alpha$ from the first neutral axis; and
an eccentric bushing arranged coaxial around the cylindrical shaft of the monoblock stem extension, the eccentric bushing comprising:
an external cylindrical shaft having a third neutral axis; and
an internal cylinder having a fourth neutral axis that is co-linear with the second neutral axis of the monoblock stem extension, wherein the third neutral axis is parallel to and offset by a distance $\beta$ from the fourth neutral axis,
wherein (a) the offset between the first neutral axis and the second neutral axis and (b) the offset between the third neutral axis and the fourth neutral axis are configured to enable independent adjustment of an antero-posterior tibial offset and a medio-lateral tibial offset,
wherein the eccentric bushing is sized and shaped to fit within an intramedullary canal of a long bone of a patient, and
wherein the eccentric bushing has a length that is greater than an outside diameter of the eccentric bushing.

4. The prosthesis system of claim 3, wherein the external cylindrical shaft of the monoblock stem extension is defined by a first length, and wherein the external cylindrical shaft of the bushing is defined by a second length.

5. The prosthesis system of claim 4, wherein the second length of the external cylindrical shaft of the bushing is shorter than the first length of the external cylindrical shaft of the monoblock stem extension.

6. The prosthesis system of claim 3, wherein the distance $\alpha$ is between about 1 mm to about 10 mm.

7. The prosthesis system of claim 3, wherein the distance $\alpha$ is between about 2 mm to about 7 mm.

8. The prosthesis system of claim 3, wherein the distance $\alpha$ is between about 3 mm to about 6 mm.

9. The prosthesis system of claim 3, wherein the distance $\beta$ is between about 0.25 mm to about 5 mm.

10. The prosthesis system of claim 3, wherein the distance $\beta$ is between about 0.50 mm to about 3 mm.

11. The prosthesis system of claim 3, wherein the distance $\beta$ is between about 1.00 mm to about 2 mm.

12. The prosthesis system of claim 3, wherein the fourth neutral axis of the internal cylinder of the bushing is configured to adjust an offset from both an antero-posterior and medio-lateral point of view.

13. The prosthesis system of claim 3, wherein the monoblock stem extension is an integral component of a prosthesis including the monoblock stem extension and at least one further element of the prosthesis system.

14. The prosthesis system of claim 3, wherein the proximal portion of the monoblock stem extension includes a first locking element for engaging a further component of the prosthesis system.

15. The prosthesis system of claim 3, wherein the monoblock stem extension is a modular component of a prosthesis including the monoblock stem extension and at least one further element of the prosthesis system.

16. The prosthesis system of claim 3 further comprising:
a baseplate having a first surface that is mountable upon bone and a second, opposed surface, the first surface including an extension member that is configured to be selectively locked with the monoblock stem extension.

17. The prosthesis system of claim 16, wherein the baseplate is a tibial tray and the monoblock stem extension is a tibial stem.

18. The prosthesis system of claim 16, wherein the extension member of the baseplate includes a boss member.

19. The prosthesis system of claim 18, wherein the boss member has internal threads.

20. The prosthesis system of claim 18, wherein the monoblock stem extension includes a threaded member matable with the boss member.

* * * * *